(12) United States Patent
Schmitz et al.

(10) Patent No.: US 6,190,870 B1
(45) Date of Patent: Feb. 20, 2001

(54) EFFICIENT ENRICHMENT AND DETECTION OF DISSEMINATED TUMOR CELLS

(75) Inventors: Jürgen Schmitz; Stefan Miltenyi, both of Bergisch Gladbach (DE); Fawn Qian, Sunnyvale, CA (US); Aaron Kantor, Newark, CA (US)

(73) Assignees: AmCell Corporation, Sunnyvale, CA (US); Miltenyi Biotec GmbH, Bergisch Gladbach (DE)

(*) Notice: Under 35 U.S.C. 154(b), the term of this patent shall be extended for 0 days.

(21) Appl. No.: 08/667,464

(22) Filed: Jun. 21, 1996

Related U.S. Application Data (63) Continuation-in-part of application No. 08/520,049, filed on Aug. 28, 1995, now abandoned.

(51) Int. Cl.[7] .................. G01N 33/553; G01N 33/574; C07K 16/30

(52) U.S. Cl. .................. 435/7.23; 435/2; 435/7.21; 435/962; 436/526; 436/64; 436/813; 436/824; 436/825; 530/388.8; 530/389.7; 530/413

(58) Field of Search .................. 436/526, 64, 808, 436/813, 824, 825; 435/7.21, 7.23, 962, 975, 2; 530/388.8, 413, 389.7

(56) References Cited

U.S. PATENT DOCUMENTS

| 4,452,773 | 6/1984 | Molday . |
| 4,770,183 | 9/1988 | Groman . |
| 4,965,204 | * 10/1990 | Civin .................. 435/430.27 |
| 5,385,707 | 1/1995 | Miltenyi et al. . |
| 5,411,863 | 5/1995 | Miltenyi . |

FOREIGN PATENT DOCUMENTS

3720844 A1 * 1/1989 (DE) .

OTHER PUBLICATIONS

Wong et al., 1995. Detection of circulating tumour cells with the magnetic activated cell sorter. British Journal of Surgery 82: 1333–37, 1995.*
Glasser et al., 1979. Neutrophil migration under agarose: quantitation and variables. Am. J. Clin. Pathol. 72: 956–62, 1979.*
Isobe et al., "Deep–etching immunogold replica eletron microscopy of cytoskeletal elements in cultured hamster heart cells," Anat. Rec., vol. 229, No. 3, pp. 415–426 (abstract only), (1991).*
Bretton et al., The Prostate, vol. 25:108 (1994).
Datta et al., J. Clin. Oncol., vol. 12:475 (1994).
Pantel, Cancer Research, vol. 53:1027–1031 (1993).
Griwatz et al., "Detection of Spreading Carcinoma Cells with Oncogene ERB B–2 Expression By Cytokeratin Antibodies and RT–PCR in the Peripheral Blood," Suppl.J.Exp.Clin.Cancer Res., vol. 13,No. 3 (Abstract),1994.

Gross et al, "Moody Study Detecting Breast Cancer Cells in Peripheral Blood Mononuclear Cells at Freqeuncies as Low as 10(–7).," P.N.A.S., vol. 92:537 (1995).
Katz et al., Urology, vol. 43:765 (1994).
Kemmer et al., J. Immunol. Methods, vol. 147: 197 (1992).
Menard et al., Br.J. Cancer, 1994.
Miltenyi et al., "High gradient magnetic cell separation with MACS, "Cytometry, vol. 11:231–238 (1990).
Molino et al., Cancer, vol. 67:1033 (1991).
Moul et al., Urology, vol. 43:68 (1994).
Oberneder et al., Urol. Res., vol. 22:3 (1994).
Osborne et al. Cancer Res., vol. 51:2706 (1991).
Redding et al., The Lancet, vol. 3:1271 (Dec. 3, 1983).
Riethmuller and Johnson, Curr. Opin. Immunol., vol. 4:647–655 (1992).
Schlimok et al., P.N.A.S., vol. 84:8672 (1987).
Schlimok et al., Eur. J. Cancer, vol. 27:1461 (1991).
Schoenfeld et al., Cancer Res., vol. 54:2986 (1994).
Seiden et al., J. Clin. Oncol., vol. 12:2634 (1994).
Shpall et al., Bone Marrow Transplantation, vol. 7:145 (1991).
Griwatz et al., "An immunological enrichment method for epithelial cells from peripheral blood," Journal of Immunological Methods, vol. 183, pp. 251–265, (1995).*
Griwatz et al., "An ultra sensitive technique for the enrichment spreading carcinoma cells in the peripheral blood," Proceedings of the American Association for Cancer Research Annual Meeting, vol. 35, Mar. 1994, p. 54, abstract 323.*
Moll et al., The Catalog of Human Cytokeratins: Patterns of Expression in Normal Epithelia, Tumors and Cultured Cells, Cell, vol. 31, pp. 11–24 (1982).*
Cote et al., "Prediction of Early Relapse in Patients With Operable Breast Cancer by Detection of Occult Bone Marrow Micrometastases," Journal of Clinical Oncology, vol. 9, No. 10, pp. 1749–1756, (1991).*
Iwao Ohtsuki, "Saponin–treatment of cells—a method for making the cytoplasmic membrane permeable to macromolecules," The Japanese Journal of Pharmacology, vol. 27 (Supplement), p. 30P, abstract 17, (1977).*

(List continued on next page.)

Primary Examiner—Christopher L. Chin
Assistant Examiner—James L. Grun
(74) Attorney, Agent, or Firm—Cooley Godward LLP (57) ABSTRACT

Tumor cells, particularly carcinoma cells, are separated from peripheral blood by magnetic sorting. The tumor cells are magnetically labeled with antibodies directed to tissue specific antigens, preferably cytoplasmic proteins. Labeling for cytoplasmic antigens is accomplished first permeabilizing, then fixing the cells. The cells are separated on a magnetic matrix. The number of tumor cells in the enriched fraction is used to calculate the number of tumor cells present in a patient hematopoietic sample.

12 Claims, 3 Drawing Sheets

OTHER PUBLICATIONS

Fenyves et al., "Cultured microvascular endothelial cells (MVEC) differ in cytoskeleton, expression of cadherins and fibronectin matrix—A study under the influence of interferon-γ," *Journal of Cell Sciences*, vol. 106, pp. 879–890, (1993).*

Martin et al., "Immunomagnetic enrichment of epithelial tumor cells from peripheral blood. A new diagnostic tool?," *Proceedings of the American Association for Cancer Research Annual Meeting*, vol. 37, Mar. 1996. p. 197, abstract 1345.*

* cited by examiner

EFFICIENT ENRICHMENT AND DETECTION OF DISSEMINATED TUMOR CELLS

This application is a continuation-in-part of application Ser. No. 08/520,049, filed Aug. 28, 1995, now abandoned.

TECHNICAL FIELD

The field of this invention is the detection of tumor cells.

BACKGROUND

One of the most serious problems that faces a practicing oncologist is the metastasis of malignant tumor cells from the primary site to multiple, distant sites. In most cases of cancer, it is the metastatic lesions that kill the patient. While surgery is often effective against a primary tumor, it cannot excise all malignant tissue if the cancer has metastasized. For example, one-third of patients with operable breast cancer develop metastases after primary therapy. Adjuvant therapy can improve this prognosis, but requires identification of high-risk patients. Staging primary tumor by size and axillary nodes status is insufficient for this purpose.

Bone and bone marrow are frequent sites of metastasis, but radiologic and scintographic techniques can detect bone involvement only when destruction of bone matrix has occurred. The presence of epithelial tumor cells in bone marrow generally correlates with conventional risk factors, such as size and histological grade of the primary carcinoma, distant metastasis and lymph node involvement. Clinical follow-up studies have demonstrated a significantly increased relapse rate in patients that presented with epithelial tumor cells in bone marrow at the time of primary surgery.

Methods are needed that allow the detection of disseminated tumor cells at a time when they have not yet developed into incurable Methods are needed that allow the detection of disseminated tumor cells at a time when they have not yet developed into incurable macrometastases. Such a diagnosis could be helpful in determining prognosis, in deciding whether a particular therapy is indicated, and in providing a way to monitor the effectiveness of therapy. Such a diagnosis might utilize the different morphology of tumor cells, as compared to normal cells of the bone and blood. Tumor specific antigens on the cell surface may be detected. Where the tumor cell is of a different developmental lineage than hematopoietic cells, for example epithelial carcinomas, then tissue specific markers may be used to identify the tumor cells.

Methods have been described for detection of spreading cancer cells into bone marrow, peripheral blood and secondary lymphoid organs from small localized primary tumors. Morphologic analysis may be performed by cytospin preparations of bone marrow smears, peripheral blood or lymph node cell samples, followed by May Grünwald-Giemsa staining and examination by light microscopy (Molino et al., 1991). Alternatively, cytospin preparations, or smears of cells, may also be stained with tumor specific or tissue specific antibodies. These methods suffer from extremely low sensitivity, and are time-consuming and laborious. As many as 100 slides might have to be examined to detect the presence of a single tumor cell.

Disseminated tumor cells have also been detected through the use of reverse transcriptase and polymerase chain reaction (RT-PCR). PCR may be used to amplify prostate specific antigen (PSA) mRNA or cytokeratin 19 mRNA. These methods have several disadvantages, particularly with respect to low sensitivity and false-positive results.

It has been shown that breast carcinoma cells can be identified or isolated from a peripheral blood sample by fluorescence activated cell sorting (Gross et al., 1995). However, the high technological effort required for FACS is a barrier to its routine use in medical diagnosis. FACS analysis or sorting is a time consuming and cost intensive procedure. Flow cytometry has the additional disadvantage in that it is difficult to sort or analyze large numbers of cells, or multiple samples at the same time.

An alternative approach to cell sorting has been described, whereby magnetic microparticles coupled to antibodies are used to select for specific cell types. Shpall et al., (1991) have described a method and a device for immunomagnetic purging of breast cancer cells from bone marrow cell samples for autologous transplantation of carcinoma patients receiving high-dose chemotherapy.

An improved magnetic sorting process whereby tumor cells could be separated from peripheral blood or other tissue sources, and which allows multiple, samples to be run on the bench would provide numerous benefits to the field of oncologic diagnosis.

Relevant Literature

Detection of disseminated tumor cells by morphology on cytospin preparations or blood smears is described in Molino et al. (1991) *Cancer* 67:1033. Use of the same technique in conjunction with antibody staining for tissue or tumor specific antigens is described in Redding et al. (1983) *The Lancet* 3:1271; Schlimok et al. (1987) *P.N.A.S.* 84:8672; Moul et al. (1994) *Urology* 43:68; Menard et al. (1994) *Br. J. Cancer;* Osborne et al. (1991) *Cancer Res.* 51:2706; Cote et al. (1991) *J. Clin. Oncol.* 9:1749; Bretton et al. (1994) *The Prostate* 25:108; and Oberneder et al. (1994) *Urol. Res.* 22:3.

Use of reverse transcriptase and the polymerase chain reaction to detect expression of tumor or tissue specific genes from samples of peripheral blood, bone marrow or lymph nodes is described in Seiden et al. (1994) *J. Clin. Oncol.* 12:2634; Katz et al. (1994) *Urology* 43:765; Schoenfeld et al. (1994) *Cancer Res.* 54:2986; and Datta et al. (1994) *J. Clin. Oncol.* 12:475.

Detection and separation of tumor cells from peripheral blood by flow cytometry is described in Gross et al. (1995) *P.N.A.S.* 92:537. Methods utilizing immunomagnetic separations are described in Shpall et al. (1991) *Bone Marrow Transplantation* 7:145; Kemmner et al. (1992) *J. Immunol. Methods* 147:197; and Griwatz et al. (1994) *Suppl. J. Exp. Clin. Cancer Res.* 13 No. 3 (Abstract).

Correlations between the presence of disseminated tumor cells in hematopoietic organs and conventional risk factors are noted in Schlimok et al. (1991) *Eur. J. Cancer* 27:1461; Huvos et al. (1971) *Ann. Surg.* 173:44; International (Ludwig) breast cancer study group (1990) *Lancet* 335:1565; and DeMascarel et al. (1992) *Br. J. Cancer* 66:523.

High gradient magnetic cell sorting is described in Miltenyi et al. (1990) *Cytometry* 11:231–238. Molday, U.S. Pat. No. 4,452,773 describes the preparation of magnetic iron-dextran microspheres and provides a summary describing the various means of preparation of particles suitable for attachment to biological materials. A description of polymeric coatings for magnetic particles used in HGMS are found in DE 3720844 (Miltenyi) and Miltenyi et al., U.S. Pat. No. 5,385,707. Methods to prepare superparamagnetic particles are described in U.S. Pat. No. 4,770,183.

SUMMARY OF THE INVENTION

Methods are provided for the identification of disseminated non-hematopoietic tumor cells from a hematopoietic cell sample, such as bone marrow, lymph or peripheral blood. The tumor cells are magnetically labeled with antibodies directed to tissue specific antigens. Labeling for cytoplasmic antigens is accomplished by a process of permeabilization and fixation of the cells. Magnetic sorting is used to separate the labeled tumor cells from the normal cells of the hematopoietic sample. The cell fraction enriched for tumor cells is useful as a source of DNA, RNA and expressed proteins, for further characterization of the metastatic cell phenotype, and for quantitating and characterizing the number of tumor cells that have disseminated from the primary tumor.

DESCRIPTION OF THE SPECIFIC EMBODIMENTS

Methods are provided that utilize magnetic sorting to identify the presence of rare disseminated tumor cells from samples of hematopoietic cells. The tumor cells are generally distant from the site of the primary tumor, and their presence in samples of patient hematopoietic cells may be indicative of the metastatic potential of the tumor. The cell sample may be treated with a permeabilizing agent and fixative in order to detect cytoplasmic proteins. Antibodies directed to tumor antigens or lineage specific antigens are used to magnetically label the tumor cells. The labeled cells are separated from unlabeled hematopoietic cells by magnetic separation. The fraction of cells enriched for tumor cells is useful for quantitating the tumor cells, and as a source of tumor cells for further characterization.

Antigens that are markers for particular cell types may be proteins, carbohydrates, lipids, or other complex biomolecules. In a few types of tumors, specific antigens have been identified that are expressed at elevated levels on the malignant cells. However, it is more common to find tumor cells that do not have distinctive antigens. In many cases, the tumor cells share many phenotypic markers with the cell type from which they originated. For example, carcinomas express antigens that are typical of epithelial cells; lymphomas of lymphocytes, etc. Such antigens may also be expressed on cells of other lineages, or may be found only at detectable levels with cells of a particular lineage, e.g. common leukocyte antigen, epithelial membrane antigen, etc. The latter are termed "tissue-specific" antigens. When tumor cells have disseminated from their tissue of origin, the tumor cells may be the only cells of that lineage present in a population of cells from a different lineage. For example, carcinomas, of epithelial origin, metastasize to the bone marrow, which is comprised of hematopoietic cells. This expression of tissue specific antigens can then be a basis for separation and detection of the tumor cells.

The dissemination of tumor cells through the hematopoietic system is medically important as an early indication of metastasis. Hematopoietic cells are developmentally derived from a common embryonic source, and share a common antigenic profile for tissue specific antigens. Sources for samples of hematopoietic cells include the blood and fractions thereof, particularly buffy coat preparations, aphoresis or leukophoresis samples; lymph and lymph nodes; and bone marrow. The term "hematopoietic cells" shall be intended to mean the normal cell populations found in blood, bone marrow, lymph, etc., and will include lymphocytes, e.g. B-cells, T-cells and natural killer cells; myeloid cells, e.g. macrophages, monocytes, polymorphonuclear cells; megakaryocytes, basophils, eosinophils, neutrophils; etc.; erythroid cells, e.g, reticulocytes, platelets and red blood cells; dendritic cells; and the progenitors thereof. Stromal and fibroblast cells found in the bone marrow are also included. The term "hematopoietic cell sample", particularly with reference to patient samples, shall be intended to include small numbers of disseminated tumor cells that may be present.

Tissue specific antigens suitable for the separation of tumor cells from hematopoietic cells are defined as antigenic molecules that are present at a detectable level in the target tumor cell, and at an undetectable level in normal hematopoietic cells, hereafter termed "separation markers". The majority of separation markers are proteins, although tumor specific mucins and carbohydrates may also find use. Usually the difference in expression level between tumor cells and hematopoietic cells will be at least about 50 fold, based on protein quantitation, more usually the difference will be at least about 500 fold or greater.

Separation markers may be cell surface antigens, or may be located in the cytoplasm of the tumor cell. Suitable markers include cytokeratins, particularly cytokeratin 8, 18 and 19, as a marker for carcinomas which are epithelial in origin, e.g. adenocarcinomas, which may have a primary tumor site in the breast, ovary, endometrium, cervix, colon, lung, pancreas, eosophagus, prostate, small bowel, rectum, uterus or stomach; and squamous cell carcinomas, which may have a primary site in the lungs, oral cavity, tongue, larynx, eosophagus, skin, bladder, cervix, eyelid, conjunctiva, vagina, etc. Epithelial membrane antigen (EMA), human embryonic antigen (HEA-125); human milk fat globules, MBr1, MBr8, Ber-EP4, 17-1A, C26 and T16 are also useful as a marker for carcinomas. Desmin and muscle-specific actin are separation markers for myogenic sarcomas. Placental alkaline phosphatase, beta-human chorionic gonadotropin, and alpha-fetoprotein are markers for trophoblastic and germ cell tumors. Prostate specific antigen is a marker for prostatic carcinomas, carcinoembryonic antigen for colon adenocarcinomas. HMB-45 is a marker for melanomas. Chromagranin-A and synaptophysin are markers for neuroendocrine and neuroectodermal tumors. Other antigens that are expressed in a tissue specific manner may also find use as separation markers. In general, the hematopoietic origin of leukemias and lymphomas precludes their separation by the subject methods, with the exception of tumors having a tumor specific antigen, e.g. specific idiotypes on B-cell or T-cell lymphomas, etc.

A hematopoietic cell sample is taken from a patient suspected of having a tumor, with possible dissemination into the blood or lymph. Preferred sites are the draining lymph nodes and lymphatics for the primary tumor site, blood, and bone marrow. Samples may be taken from aphoresis patients being treated to mobilize hematopoietic progenitor cells. Blood samples will usually be from about 5 to 100 ml of whole blood, and may be treated with anticoagulants, e.g. heparin, EDTA, citrate, acid citrate dextrose or citrate phosphate dextrose, as known in the art. Blood samples may be further fractioned to enrich for the buffy coat fraction. Bone marrow aspirations may be performed on iliac crest, sternum, etc., and treated with anticoagulants. The sample may be subjected to treatment such as dilution in buffered medium, concentration, filtration, or other gross treatment that will not involve any specific separation.

Suitable samples will have at least about $10^6$ of nucleated cells, usually at least about $10^7$, and preferably $10^8$. Detection of tumor cells can be achieved when the tumor cells comprise at least about 1 cell per $10^7$ hematopoietic cells.

A preparation of nucleated cells may be made from the sample using a procedure that can separate nucleated cells from erythrocytes. The use of FicoII-Paque density gradients or elutriation for such separations is well documented in the literature. Alternatively, the blood cells may be resuspended in a solution which selectively lyses erythrocytes, e.g. ammonium chloride-potassium; ammonium oxalate; etc., or whole blood may be used. The cells may also be resuspended in a solution of saponin, which complexes with membrane cholesterol and other unconjugated β-hydroxysterols, leading to the formation of pores in the cell membrane. All cells are permeabilized, and the erythrocytes release hemoglobin. The erythrocytes ghosts are then separated from nucleated cells by centrifugation.

The sample of hematopoietic cells is selectively enriched for tumor cells. Reagents that specifically bind tumor separation markers, as previously described, are attached to colloidal superparamagnetic particles. Especially useful reagents are antibodies specific for the tumor separation markers. Whole antibodies may be used, or fragments, e.g., Fab, F(ab')$_2$, light or heavy chain fragments, etc. Such separation antibodies may be polyclonal or monoclonal and are generally commercially available or alternatively, readily produced by techniques known to those skilled in the art. Antibodies selected for use will have a low level of non-specific staining of hematopoietic cells and will usually have an affinity of at least about 100 $\mu$M for the antigen.

In one embodiment of the invention, the separation antibodies are coupled to a magnetic reagent, such as a superparamagnetic microparticle (microparticle). Herein incorporated by reference, Molday (U.S. Pat. No. 4,452,773) describes the preparation of magnetic iron-dextran microparticles and provides a summary describing the various means of preparing particles suitable for attachment to biological materials. A description of polymeric coatings for magnetic particles used in high gradient magnetic separation (HGMS) methods are found in DE 3720844 (Miltenyi) and U.S. Pat. No. 5,385,707. Methods to prepare superparamagnetic particles are described in U.S. Pat. No. 4,770,183. The microparticles will usually be less than about 100 nm in diameter, and usually will be greater than about 10 nm in diameter. The exact method for coupling is not critical to the practice of the invention, and a number of alternatives are known in the art. Direct coupling attaches the separation antibodies to the particles. Indirect coupling can be accomplished by several methods. The antibodies may be coupled to one member of a high affinity binding system, e.g. biotin, and the particles attached to the other member, e.g. avidin. One may also use second stage antibodies that recognize species-specific epitopes of the antibodies, e.g. anti-mouse Ig, anti-rat Ig, etc. Indirect coupling methods allow the use of a single magnetically coupled entity, e.g. antibody, avidin, etc., with a variety of separation antibodies.

One preferred method uses hapten-specific second stage antibodies coupled to the magnetic particles, as described in co-pending patent application Ser. No. 08/252,112. The hapten specific antibodies will usually have an affinity of at least about 100 $\mu$M for the hapten. The antibodies are conjugated to the appropriate hapten. Suitable haptens include digoxin, digoxigenin, FITC, dinitrophenyl, nitrophenyl, etc. Methods for conjugation of the hapten to antibody are known in the art.

While not necessary for practice of the subject methods, it may be useful to treat the cells during the initial staining with immunocytochemistry reagents. Such reagents are frequently labeled antibodies that are used for identification of tumor cells in the enriched cell preparation, herein analysis antibodies. These may include enzyme conjugated antibodies, e.g. horseradish peroxidase, phosphatase, etc., haptenated antibodies, e.g. biotin conjugates, digoxigenin conjugates, etc. or with a fluorochrome conjugated antibody, e.g. phycoerythrin, FITC, rhodamine, Texas red, allophycocyanin, etc. The analysis antibodies may have specificity for any of the tumor antigens previously described, or may be specific for markers expressed on hematopoietic cells. Reagents may also include blocking agents that reduce non-specific labeling, e.g. Fc receptor blocking reagent, peroxidase blocking reagent, etc. Labeling may conveniently utilize the same indirect coupling system as the magnetic particles. For example, a cocktail of digoxigenin-coupled antibodies may be used in combination with anti-digoxigenin antibody coupled to magnetic particles, followed by labeling with a fluorochrome conjugated antibody directed to the anti-hapten antibody. Conveniently, a non-magnetic, fluorochrome-conjugated antibody specific for a hematopoietic cell marker, e.g. CD45, etc. is included in the labeling, and used for analysis after the separation.

The analysis antibodies may be used to monitor the cell composition after the separation steps are performed, by any convenient method, e.g. microscopically, flow cytometry, etc. In one embodiment of the invention, the cells are directly captured on a microscope slide, or a filter, e.g. a polycarbonate filter, for immunocytochemistry analysis. The direct capture is advantageous because there is decreased cell loss through processing steps.

As previously described, separation markers may be found on the cell surface, or in the cytoplasm, including the nuclear membrane, of the tumor cells. Where the separation marker is cytoplasmically located, it is necessary to permeabilize and fix the cells before binding to the separation antibodies. It has been found to be advantageous to permeabilize the cells before fixation. The cells are resuspended in staining medium, which can be any medium that maintains the morphology of the cells. Various media are commercially available and may be used according to the nature of the cells, including Dulbecco's Modified Eagle Medium (DMEM), Hank's Balanced Salt Solution (HBSS), Dulbecco's phosphate buffered saline (DPBS), RPMI, Iscove's medium, PBS with 5 mM EDTA, etc. A preferred medium is phosphate buffered saline. Permeabilizing agents are known in the art, and include mild detergents, such as Triton X-100, NP-40, saponin, etc. A preferred permeabilizing agent is saponin at a concentration of from about 0.01 to 0.5%.

A solution of fixative is then added to the cell suspension. Various fixatives are known in the art, including formaldehyde, paraformaldehyde, formaldehyde/acetone, methanol/acetone, etc. Formaldehyde used at a final concentration of about 1 to 2% has been found to be a good cross-linking fixative. Where saponin is the permeabilizing agent, it is included in all subsequent incubation and washing steps for intracellular antibody labeling, at a concentration of from about 0.1 to 2%.

The separation antibodies are added to the suspension of hematopoietic cells, and incubated for a period of time sufficient to bind the available antigens. The incubation will usually be at least about 2 minutes and usually less than about 30 minutes. It is desirable to have a sufficient concentration of antibodies in the reaction mixture so that the efficiency of the magnetic separation is not limited by lack of antibody. The appropriate concentration is determined by titration.

Where a second stage magnetically coupled antibody is used, the cell suspension may be washed and resuspended in medium as described above prior to incubation with the second stage antibodies. Alternatively, the second stage antibody may be added directly into the reaction mix. When directly coupled separation antibodies are used, the cell suspension may be used directly in the next step, or washed and resuspended in medium.

The suspension of cells is applied to a separation device. Exemplary magnetic separation devices are described in WO/90/07380, PCT/US96/00953 and EP 438,520, herein incorporated by reference. In a preferred embodiment, an improvement is provided by the use of a high gradient magnetic matrix of closely packed ferromagnetic spheres in place of the prior art matrix of steel wool, wires, etc. The spheres will be usually at least about 200 $\mu$m in diameter and not more than about 1000 $\mu$m in diameter, more usually at least about 250 $\mu$m in diameter and not more than about 300 $\mu$m in diameter. For optimum performance it is preferred that the composition of spheres be generally homogeneous in size, usually varying not more than about 15% from the average size. The spheres are composed of a ferromagnetic material (e.g. iron, steel, etc.), which may be coated with an impermeable coating to prevent the contact of cells with metal. By impermeable coating it is meant a polymeric coating which contains substantially less than 30% water by weight, which does not permit the passage of ions, and which is formed on the sphere as a result of passive application, cross-linking or polymerization of a relatively hydrophobic polymer or co-polymer. Suitable polymers include polystyrenes, polyacrylamides, polyetherurethanes, polysulfones, fluorinated or chlorinated polymers such as polyvinyl chloride, polyethylenes and polypropylenes, polycarbonates and polyesters, etc. The matrix of spheres should have adequate surface area to create sufficient magnetic field gradients in the separation device to permit efficient retention of magnetically labeled cells. The volume necessary for a given separation may be empirically determined, and will vary with the cell size, antigen density on the cell surface, antibody affinity, etc. The flow rate will be determined by the size of the column, but will generally not require a cannula or valve to regulate the flow.

The labeled cells are retained in the magnetic separation device in the presence of a magnetic field, usually at least about 100 mT, more usually at least about 500 mT, usually not more than about 2 T, more usually not more than about 1 T. The source of the magnetic field may be a permanent or electromagnet. After the initial binding, the device may be washed with any suitable physiological buffer to remove unbound cells.

The unbound cells contained in the eluate are collected as the eluate passes through the column. The bound cells, containing the tumor cells, are released by removing the magnetic field, and eluting in a suitable buffer. The cells may be collected in any appropriate medium. Various media are commercially available and may be used according to the nature of the cells, including dMEM, HBSS, dPBS, RPMI, PBS-EDTA, PBS. Iscove's medium, etc., frequently supplemented with fetal calf serum, BSA, HSA, etc.

In many cases a single separation step will provide sufficient enrichment of tumor cells. The actual efficiency will depend on the particular separation markers and antibodies that are used, and the concentration of tumor cells in the sample. For example, in controlled experiments using cytokeratin as a marker for carcinoma cells, at least about 25%, more usually at least about 50% of the tumor cells are recovered.

Where greater purity is desired, additional separation steps may be performed. The eluted, magnetic fraction may be passed over a second magnetic column to reduce the number of non-specifically bound cells. Higher purity of tumor cells is also obtained by performing two enrichment steps, using two different tumor specific separation markers. Alternatively, a multiparameter separation may be performed, by depleting hematopoietic cells from the sample. Suitable markers for depletion are antigens that are widely expressed on hematopoietic cells and absent on the target tumor cells, e.g. CD45, etc. The depletion step may be performed first, followed by the enrichment step. The depletion is performed essentially as described for the enrichment, except that the non-magnetic fraction is collected. The enrichment is then performed on the leukocyte depleted fraction.

If the enrichment step is to be performed first, then an additional step is necessary after the enrichment, in order to remove the magnetic label from the enriched cells. This may be accomplished by any suitable method. For example, the enriched cell population may be incubated with a solution of dextranase, where the dextranase is present at a concentration sufficient to remove substantially all microparticles from the labeled cells. Usually the reaction will be complete in at least about 15 minutes. The depletion step may then be performed as previously described with the dextranase treated cells. Another method if removing the magnetic label uses 3-(2-pyridyldithio)propionic acid N-hydroxysuccinimide ester (SPDP) as a dithiothreitol (DTT) cleavable linker.

Alternatively, the enrichment step may be performed first, and the depletion step modified to use large magnetic spheres in place of the microparticles. The use of such magnetic spheres has been previously described, and the reagents are commercially available. The enriched cell population is incubated with highly magnetic polymer spheres of about 1 to 10 $\mu$m diameter conjugated to the depletion antibody cocktail. The mixture of cells is then placed in close proximity to a magnetic field. Substantially all cells bound to the polymer spheres are bound to the magnet within about 1 minute, and not more than about 5 minutes. The unbound cells may be decanted and used.

A single separation step will generally provide a sufficient enrichment of tumor cells for quantitation by microscopic or cytometric analysis. The tumor cells in the enriched fraction may be quantitated by morphology, immunohistochemistry, staining with fluorochrome conjugated antibodies that distinguish between tumor cells and hematopoietic cells, and other techniques as known in the art. A counterstain specific for hematopoietic cells may conveniently be included. A control sample artificially "spiked" with defined numbers of tumor cells may be used as a control to calculate the percent recovery of tumor cells. This information may be used to determine the number of tumor cells present in the original patient sample.

The tumor cells may be further characterized as to their phenotype by PCR, ELISA, FISH, in situ FISH, competitive hybridization, chromosome painting, immunohistochemistry, etc. The expression of a number of proteins related to malignancy is of interest, including oncogenes, e.g. sis, src, yes, fgr, Ick, abl, erbB, neu, fms, ras, mos, myc, myb, p53, fos, jun, rel, etc.; drug resistance proteins, e.g. DHFR, p-glycoprotein, etc.; metastatic factors, e.g. metalloproteases, integrins, angiogenic factors, cathepsin B, etc.; and other characteristics indicative of the growth, metastatic potential and drug resistance of the tumor cell. The cell cycle status and DNA content of the tumor cells is also of interest.

Methods that utilize the polymerase chain reaction (PCR) are of interest. DNA or RNA is isolated from the cell sample, and PCR used to amplify a region of the RNA or DNA by the use of specific primers. The amplification product is then analyzed for the presence of specific alleles. The analysis may fractionate the amplification product according to size to determine fragment length polymorphisms, or may use hybridization to determine the absence or presence of a specific sequence. A pre-amplification step (PEP) with specific or non-specific primers may be used. Bulk PCR, where DNA or RNA from a number of cells is amplified in a single reaction may be used to detect the presence of chromosomal translocations, oncogene expression, etc. Isolated single cells may also amplified by PCR, usually in combination with a pre-amplification step.

Amplification of DNA allows detection of gene amplification, chromosomal translocations, gene mutations in coding regions or regulatory sequences, chromosomal aneuploidies, viral DNA, RFLPs, etc. Amplification of RNA allows determination of the expression of genes such as oncogenes, tumor suppressor genes, cyclins, kinases, regulatory DNA binding proteins, growth factors, receptors, viral proteins, adhesion molecules, inhibitors, etc., and detection of variant alleles of expressed genes. FISH allows the detection of gene amplification, chromosomal translocations, gene mutations, chromosomal aneuploidies, viral DNA, etc.

In order to address the needs of a clinical laboratory, a kit may be provided having the reagents and apparatus necessary to perform the subject invention. Such a kit may contain hapten conjugated separation marker specific antibodies, e.g. anti-cytokeratin, anti-EMA, etc.; anti-hapten antibody conjugated to superparamagnetic particles; separation marker specific antibodies directly conjugated to superparamagnetic particles, and column(s) suitable for selection, particularly columns prepacked with ferromagnetic spheres. Components may also include superparamagnetically coupled leukocyte specific antibody, e.g. anti-CD45, etc. For convenience, buffers may be included for erythrocyte lysis, cell fixation and permeabilization, cell staining and collection, etc. While single columns may be used, it is anticipated that multiple columns will be run simultaneously, and an apparatus for automated or manual procedures may be provided for such a purpose.

The following examples are offered by way of illustration and not by way of limitation.

EXPERIMENTAL

EXAMPLE 1

Immunomagnetic separation of breast cancer cells from artificial mixtures of blood cells and breast cancer cells by high-gradient magnetic cell sorting using an anti cytokeratin 8/18 antibody chemically linked to colloidal superparamagnetic microparticles.

Material and Methods

Cell sample preparation. Leukocyte-rich buffy coats were prepared from anticoagulant treated peripheral blood of a healthy donor by centrifugation at 400×g. Four samples of 5 ml of buffy coat were mixed with 30.000, 3000, 300 and 0 cells of the mammary carcinoma cell line SK-BR-3.

Erythrocyte lysis and permeabilization of nucleated cells. Cells were incubated in phosphate-buffered saline (PBS) and 0.1% saponin (erythrocyte lysis/cytokeratin unmasking solution) for 5 min at room temperature.

Fixation. Cells were fixed in PBS, 0.05% saponin and 2% formaldehyde for 30 minutes at room temperature and washed once in PBS with 0.5% BSA and 0.5% saponin (PBS/BSA/saponin buffer)

Magnetic labeling of cytokeratin 8/18-expressing cells. Cells were incubated with anti-cytokeratin 8/18 mAb-conjugated colloidal superparamagnetic microbeads in PBS/BSA/saponin buffer for 35 minutes at room temperature (Moll et al. (1982) *Cell* 31:11). Afterwards, anti-cytokeratin 8/18 mAb-conjugated to PE and biotinylated HEA-125 mAb were added and the cells were incubated for further 10 minutes at room temperature. Cells were washed in PBS/BSA/saponin buffer and stained with CD45-FITC and streptavidin-CyChrome for 10 minutes at room temperature in PBS/BSA/saponin buffer.

Positive selection of cytokeratin 8/18-expressing cells by high-gradient magnetic cell sorting (HGMS). Magnetically labeled cytokeratin 8/18-expressing cells were enriched by two sequential positive selections on MiniMACS columns (magnetizable steelball matrix, Miltenyi Biotec GmbH, Bergisch Gladbach) inserted in a MiniMACS permanent magnet.

Flow cytometric analysis. To evaluate the efficiency of the magnetic enrichment of cytokeratin 8/18-expressing SK-BR-3 cells, aliquots of unseparated cells, magnetic and nonmagnetic cell fractions were analyzed by flow cytometry using a FACScan (Becton Dickinson). Data of 5000–17000 cells were collected and analyzed using FACScan Research Software (Becton Dickinson) or CellQuest (Becton Dickinson), shown in Table 1.

TABLE 1

| | | | | |
|---|---|---|---|---|
| No. of SK-BR-3 cells added | 30,000 | 3,000 | 300 | 0 |
| No. of leukocytes (5 ml buffy coat) | $7.8 \times 10^7$ | $9.2 \times 10^7$ | $8.9 \times 10^7$ | $8.9 \times 10^7$ |
| recovered SK-BR-3 cells | 21,500 | 2,070 | 148 | 0 |
| recovery (%) | 72 | 69 | 49 | — |
| frequency of SK-BR-3 cells in enriched fraction (%) | 24.8 | 4.7 | 1.01 | 0.00 |
| enrichment factor | 857 | 1513 | 3027 | — |

Figure 1A:
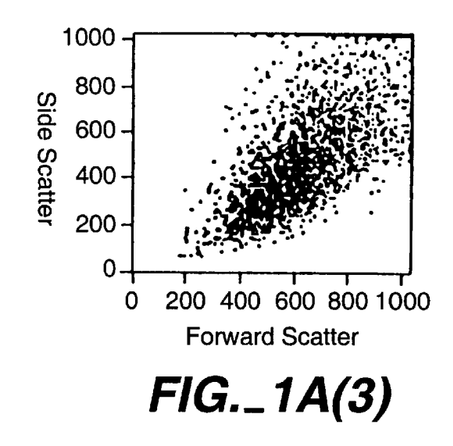
FIGS. 1A to 1D show the characterization of human epithelial antigen (HEA) and cytokeratin 8/18 expression during the magnetic enrichment of experimentally added breast carcinoma cells from a sample of leucocyte-rich buffy coat cells.
Figure 1B:
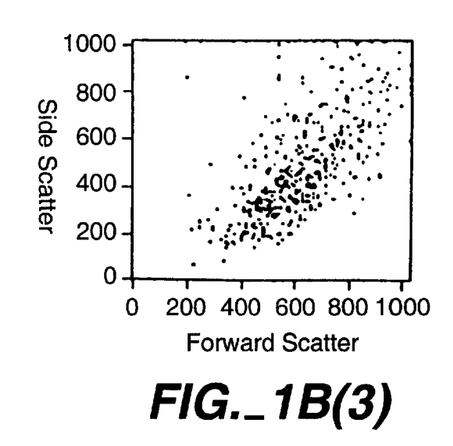
Figure 1C:
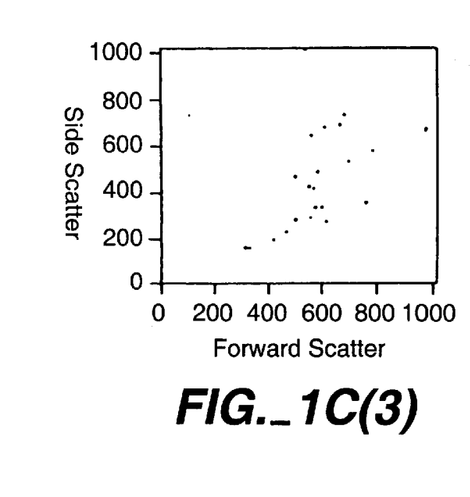
Figure 1D:
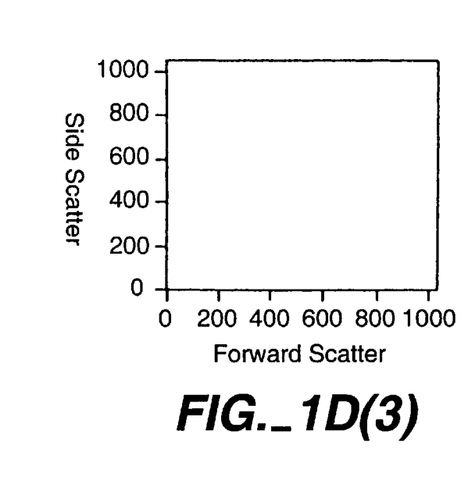

FIGS. 1A(1) to 1D(1) show HEA-125-Cychrome vs. cytokeratin 8/18-PE staining of cells from a leukocyte-rich buffy coats containing about $10^8$ leukocytes mixed with 30,000 (FIG. 1A(1), 3000 (FIG. 1B(1), 300 (FIG. 1C(1)) and 0 (FIG. 1D(1)) cells of the mammary carcinoma cell line SK-BR-3. The frequencies of cancer cells in the counting window (R1) are indicated. FIGS. 1A(2) to 1D(2) show HEA-125-Cychrome vs. cytokeratin 8/18-PE staining of the same cell samples after magnetic enrichment of cytokeratin 8/18-expressing SK-BR-3 cells. The frequencies of cancer cells in the counting windows (R1) are indicated. FIGS. 1A(3) to 1D(3) show the light-scatter properties of the enriched cytokeratin 8/18-expressing SK-BR-3 cells gated (gate R1) in FIGS. 1A(2) to 1D(2).

EXAMPLE 2

Immunomagnetic enrichment of tumor cells from peripheral blood of breast cancer patients (M1 patients) by high-gradient magnetic cells sorting using an anti-cytokeratin 8/18 antibody chemically linked to colloidal superparamagnetic microparticles.

Material and Methods

Cell sample preparation. Leukocyte-rich buffy coats were prepared from 30–40 ml freshly drawn anticoagulant-treated peripheral blood of breast cancer patients with distant metastases. Blood was transferred to a clean 50 ml conical tube, and phosphate-buffered saline (PBS) added to a final volume of 50 ml. The sample was centrifuged at 400×g for 35 min (no brake). The upper plasma layer was discarded, and the white cell layer transferred (about 5 ml) to a clean 50 ml conical tube. 5 ml samples of buffy coats from normal donors were used for negative controls. $2.8 \times 10^4$ cells of the breast carcinoma cell line BT474 were added to a 5 ml buffy coat from a healthy donor for a positive control. Erythrocyte lysis, permeabilization of nucleated cells and fixation was performed as described for Example 1.

Magnetic labeling of cytokeratin 8/18-expressing cells. Cells were incubated with anti-cytokeratin 8/18 mAb-conjugated colloidal superparamagnetic microbeads in PBS/BSA/saponin buffer for 35–45 minutes at room temperature. Afterwards, anti-cytokeratin 8/18 mAb-conjugated to PE and biotinylated anti-HEA-125 mAb or biotinylated CD45 mAb were added and the cells were washed in PBS/BSA/saponin buffer and stained with streptavidin-CyChrome (and CD45-FITC, if the cells were stained with biotinylated anti-HEA-125 mAb) for 10–15 minutes at room temperature in PBS/BSA/saponin buffer.

Positive selection of cytokeratin 8/18-expressing cells by high-gradient magnetic cell sorting (HGMS). Magnetically labeled cytokeratin 8/18-expressing cells were enriched by two sequential positive selections on MiniMACS columns (magnetizable steelball matrix, Miltenyi Biotec GmbH, Bergisch Gladbach) inserted in a MiniMACS permanent magnet.

Flow cytometric analysis. To evaluate the efficiency of the magnetic enrichment of cytokeratin 8/18-expressing cells, aliquots of unseparated cells and from the magnetic and nonmagnetic cell fractions were analyzed by flow cytometry using a FACScan (Becton Dickinson). Data of 5000–17000 cells were collected and analyzed using FACScan Research Software (Becton Dickinson) or CellQuest (Becton Dickinson).

Results

Figure 2A:
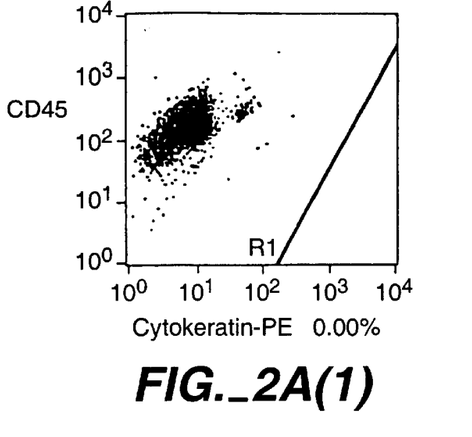
FIGS. 2A to 2C show the characterization of CD45 and cytokeratin 8/18 expression during the magnetic enrichment of tumor cells from a leucocyte-rich buffy coat fraction of peripheral blood from a breast cancer patient with distant metastases, or from control samples.
Figure 2B:
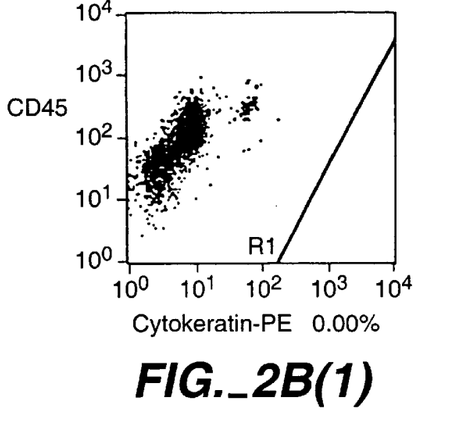
Figure 2C:
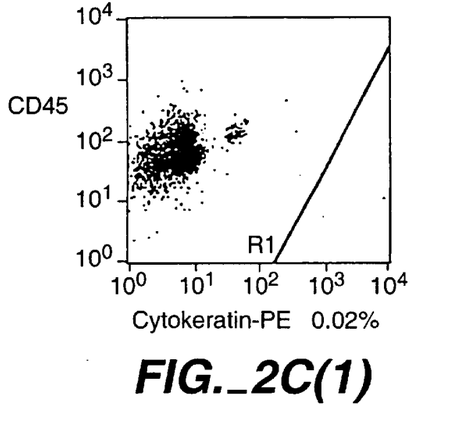

The analysis from Patient 1 is shown in FIG. 2B(1) and 2B(2). FIGS. 2A(1) to 2C(1) show CD45-Cychrome vs. cytokeratin 8/18-PE staining of cells from a leucocyte-rich buffy coat of a healthy donor (FIG. 2A(1)), of cells from a leucocyte-rich buffy coat of a breast cancer patient with distant metastases (FIG. 2B(1)) and of cells from a leucocyte-rich buffy coat of a healthy donor mixed with cells from a mammary carcinoma cell line BT474 (FIG. 2C(1)). 28,000 BT474 cells were mixed with a buffy coat containing about $1.5 \times 10^8$ leucocytes. The frequencies of cancer cells in the counting windows (R1) are indicated. FIGS. 2A(2) to 2C(2) show CD45-Cychrome vs. cytokeratin 8/18-PE staining of the same cell samples after magnetic enrichment of cytokeratin 8/18-expressing cancer cells. The frequencies of cancer cells in the counting windows (R1) are indicated.

Cytokeratin 8/18-expressing tumor cells were enriched to a frequency of 11.7% (FIG. 2B(2)). About 3,110 cytokeratin 8/18-expressing cancer cells were enriched from 38 ml of blood ($2.56 \times 10^8$ leukocytes). This corresponds to a frequency of $1.21 \times 10^{-5}$.

The results from a healthy donor are shown in FIGS. 2A(1) and 2A(2)). No cytokeratin 8/18-expressing cell was enriched from the 5 ml buffy coat cell sample ($1.54 \times 10^8$ leukocytes) of the normal healthy donor 1. One cytokeratin 8/18-expressing cell was enriched from the 5 ml buffy coat cell sample ($1.54 \times 10^8$ leukocytes) of the healthy donor 2.

Cytokeratin 8/18-expressing tumor cells from patient 2 were enriched to a frequency of 12.5%, with about 10,800 cytokeratin 8/18-expressing cancer cells enriched from 30 ml of blood ($1.92 \times 10^8$ leukocytes). This corresponds to a original sample tumor cell frequency of $5.63 \times 10^{-5}$. According to light-scatter properties, the breast cancer cells are larger than lymphocytes, and even monocytes. Staining for the epithelial cell-specific surface antigen HEA-125 showed a considerable heterogeneity in the expression level on the tumor cells.

Patient 3 was undergoing irradiation therapy at the time of the experiments. Cytokeratin 8/18-expressing tumor cells were enriched by the separation procedure to a frequency of 0.51%. About 68 cytokeratin 8/18-expressing cancer cells were enriched from 30 ml of blood ($5.68 \times 10^7$ leukocytes). This corresponds to a frequency in the original sample of 1 tumor cell per $8.4 \times 10^5$ leukocytes.

The data in Table 2 summarizes the results of tumor cell enrichment from breast carcinoma patients.

TABLE 2

| Patient | 1 | 2 | 3 | 4 | 5 | 6 |
|---|---|---|---|---|---|---|
| No. CK 8/18+ cells* | 3,110 | 10,800 | 68 | 32 | 9 | 76 |
| Frequency CK 8/18+ cells in enriched fraction | 11.70 | 12.50 | 0.51 | 0.08 | 0.02 | 0.35 |
| ml of blood in sample | 38 | 30 | 30 | 40 | 35 | 39 |
| Leukocytes in sample | $2.5 \times 10^8$ | $1.92 \times 10^8$ | $5.68 \times 10^7$ | $1.47 \times 10^8$ | $1.2 \times 10^8$ | $6.76 \times 10^7$ |
| Frequency CK 8/18+ cells in blood sample | $1.21 \times 10^{-5}$ | $5.63 \times 10^{-5}$ | $1.19 \times 10^{-6}$ | $2.18 \times 10^{-7}$ | $7.5 \times 10^{-8}$ | $1.12 \times 10^{-6}$ |

*CK 8/18+ designates cells positive for cytokeratin 8/18 by cytoplasmic staining.

EXAMPLE 3

Comparative immunomagnetic isolation of breast cancer cells from artificial mixtures of blood cells and breast cancer cells by high-gradient magnetic cell sorting using either an anti cytokeratin 8/18 mAb or the HEA-125 mAb chemically linked to colloidal superparamagnetic microparticles.

Material and Methods

1. Cell sample preparation. Leukocyte-rich buffy coats were prepared from anticoagulated-treated peripheral blood of a healthy donor by centrifugation at 400×g. Two samples of 5 ml of buffy coat were mixed with 20000 cells of the mammary carcinoma cell line BT474. Erythrocyte lysis, permeabilization and fixation were performed as described for Example 1.

Magnetic labeling. Cells were incubated either with anti cytokeratin 8/18 mAb-conjugated colloidal superparamagnetic microbeads or HEA-125 mAb-conjugated colloidal superparamagnetic microbeads in PBS/BSA/saponin buffer for 45 minutes at room temperature. Afterwards, anti cytokeratin 8/18 mAb-conjugated to PE and biotinylated HEA-125 mAb were added and the cells were incubated for further 15 minutes at room temperature. Cells were washed in PBS/BSA/saponin buffer and stained with CD45-FITC and streptavidin-CyChrome for 15 minutes at room temperature in PBS/BSA/saponin buffer.

Positive selection of cytokeratin 8/18-expressing cells by high-gradient magnetic cell sorting (HGMS). Magnetically labeled cytokeratin 8/18-expressing cells were enriched by two sequential positive selections on MiniMACS columns inserted in a MiniMACS permanent magnet.

Flow cytometric analysis. To evaluate the efficiency of the magnetic enrichment of BT474 cells, aliquots of unseparated cells and from the magnetic and nonmagnetic cell fractions were analyzed by flow cytometry using a FACScan (Becton Dickinson). Data of 5000–17000 cells were collected and analyzed using FACScan Research Software (Becton Dickinson) or Cell Quest (Becton Dickinson).

Results

BT474 cells isolated using anti-cytokeratin antibodies were enriched to a frequency of 7.05%. About 4200 BT474 cells were enriched from 5 ml buffy coat ($5.26 \times 10^7$ leukocytes), with a recovery rate of 21%. A background level of one "positive cell" was detected in the control separation of 5 ml buffy coat without added cancer cells.

BT474 cells isolated anti-HEA-125 antibodies were enriched to a frequency of 26.03%. About 3890 BT474 cells were enriched from 5 ml buffy coat ($8.68 \times 10^7$ leukocytes), with a recovery rate of 19.5%. No "positive cells" were detected in the control separation of 5 ml buffy coat without added cancer cells.

The procedure was repeated with two different samples of 0.3 ml of buffy coat, mixed with 50,000 cells of the mammary carcinoma cell lines BT474 and SK-BR-3, but no permeabilization and fixation was performed. The live cells were incubated with HEA-125 mAb-conjugated colloidal superparamagnetic microbeads in PBS/BSA for 20 minutes at room temperature. Afterwards, HEA-125-FITC were added and the cells were incubated for further 10 minutes at room temperature.

Viable SK-BR-3 cells were enriched from a frequency of 4.73% in the starting population to a frequency of 81.84%. About 20,800 SK-BR-3 cells were recovered from 0.3 ml buffy coat ($6.18 \times 10^6$ leukocytes), with a recovery rate of 42%. Viable BT474 cells were enriched from a frequency of 5.28% to a frequency of 81.39%. About 22,000 SK-BR-3 cells were recovered from 0.3 ml buffy coat ($7.45 \times 10^6$ leukocytes), giving a recovery rate of 44%.

EXAMPLE 4

Detection of cancer cells from whole blood, without ficoll isolation of buffy coat cells, was performed. This procedure reduced the risk of losing tumor cells. At least 40% more tumor cells were detected in the patients with the whole blood method, rather than with the buffy coat isolation method. Moreover, the process of tumor cell detection was shortened 30 min. by eliminating the step of isolation of buffy coat. Tumor cells were detected by directly capturing enriched cells on a filter, followed by quantitation with immunocytochemistry.

Materials and Methods

Tumor cell enrichment. Nucleated cells in whole blood are counted by diluting an aliquot of cells 1:10 with BSA solution (phosphate buffered saline with 1% BSA, 5 mM EDTA, 0.05% procline-300, 0.01% F68, pH 7.4). 10 $\mu$l of the dilution is mixed with an equal volume of ethidium bromide/acridine orange dye. Live nucleated cells show up under a flourescence microscope as green colored.

An aliquot of whole blood that contains $10^8$ nucleated cells is placed in a tube, and DNAse I added to a final concentration of 100 U/ml. The blood is centrifuged at 400 g for 10 min. at room temperature. The plasma is carefully removed without disturbing the interface. BSA solution is added to a total volume of 45 ml. per tube, and 0.9 ml of saponin solution (5% saponin in PBS with 0.05% sodium azide). Incubate the cell suspension for exactly five minutes at room temperature. Add 2.5 ml 37% formaldehyde, mix well and incubate for 30 minutes at room temperature. Centrifuge cell suspension at 250 g for 5 minutes. Aspirate supernatant, resuspend the cells in 30 ml of staining solution (0.5% saponin in BSA solution). Centrifuge at 250 g for 5 minutes, aspirate supernatant and resuspend in 10 ml of staining solution. Centrifuge at 250 g for 5 minutes, aspirate supernatant.

Resuspend the cells in 200 $\mu$l of the peroxidase blocking reagent (0.03% hydrogen peroxide containing 0.05% sodium azide) for 5 minutes at room temperature. Add 5 ml of the staining solution and centrifuge for 5 min. at 250 g. Aspirate supernatant and resuspend cells in 600 $\mu$l of BSA solution. Add 200 $\mu$l of FcR blocking reagent (5 mg/ml rabbit IgG in BSA solution, 0.05% procline-300). Add 200 $\mu$l of antibody (Cam5.2 anti-cytokeratin antibody conjugated to magnetic microparticles). Incubate at room temperature for 45 minutes. Add 5 ml of staining solution and centrifuge at 250 g for 5 min. Aspirate supernatant, resuspend the cells in a polymer solution (peroxidase labeled polyer conjugated to goat anti-mouse Ig in Tris-HCl buffer, Dako Corp.) and incubate at room temperature for 30 minutes. Add 5 ml of blocking solution and centrifuge at 250 g for 5 minutes. Aspirate supernatant, resuspend the cells in 1 ml of degassed BSA buffer.

Prepare a mini-MACS column (Miltenyi Biotec GmbH) by placing in a magnetic field and rinsing the column twice with 2 ml of degassed BSA solution. Load 1 ml of cell suspension into the column, collect the negative fraction (if desired). Rinse the tube with an additional 1 ml of BSA solution, and load onto the column. When the column has finished dripping, load 2 ml of degassed BSA solution into the column to wash away the non-specifically bound cells.

Prepare a filter holder (Poretics) and 2 micron polycarbonate filter (Poretics) to receive the cells. Screw the two parts of the holder tightly, and push 5 ml of BSA buffer through the filter to wet it and check for leaks. Screw the filter holder onto the syringe and place in a modified 50 ml conical tube. Place the mini-MACS column containing the bound cells into the syringe. Place the complex into a centrifuge. Load 2 ml of degassed BSA solution into the column. Centrifuge at 1,250 g for 5 minutes. Discard the column, and wash the filter with an additional 10 ml of BSA solution. Remove the filter and holder from the complex.

Load 180 μl of AEC buffer (3-amino-9-ethylcarbazole in N,N-9(DMF) and acetate buffer, pH 5.0, containing hydrogen peroxide, enhancers, stabilizers and anti-microbial reagent) along one side of the wall of the holder. Incubate at room temperature for 5 minutes. Wash by centrifugation with 10 ml of BSA buffer, as previously performed.

Place a drop of mounting medium (aqueous-based mounting medium, Dako) on a cyto-clear slide. Place the filter on the mounting medium, and add another drop on top. Coverslip and remove air bubbles. Read the slide under a normal light microscope with 10× magnification. The tumor cells are stained bright red, and normal peripheral blood are transparent.

Results

Tests for the detection of cancer cells in nineteen blood samples from sixteen breast cancer patients with stage IV diseases were performed. Among these patients, fifteen were peripheral blood samples and four were leukopheresis samples. The sensitivity of tumor cell detection in the patients' samples reaches 1 tumor cell in $10^8$ PBMC, or 1 tumor cell in 10–20 ml of whole blood. No tumor cells were detected in any of the eight healthy individuals. Tumor cells were detected in 79% of the patient samples. The range of cancer cells detected in patients who had stage IV disease, and had been through intensive chemotherapy, was from 0.5 to 80 tumor cells in 10 ml of blood or 1 to 60 tumor cells in $10^8$ nucleated cells. A filter capture method for tumor cell detection was shown to provide for efficient and consistent tumor cell capture.

In the experiments described in Examples 1 to 3, the methods started with isolation of buffy coat cells as a first step. To investigate whether this step was responsible for the loss of nucleated cells, which include both WBC and tumor cells, the nucleated cells in both whole blood and buffy coat isolated from the whole blood were counted with a hemacytometer under a fluorescent microscope after staining with ethidium bromide/acridine orange. The results showed that a buffy coat isolation step could lose about 3% of total nucleated cells, as shown in the Table 3. A comparison of tumor cell detection in the whole blood and in the buffy coat of the same patient was also performed. The result showed that at least 40% more tumor cells were detected with the whole blood method than with the buffy coat isolation method, shown in Table 4. The complete process of tumor cell detection was shortened 30 min. by elimination of this step.

A filter capture method used a polycarbonate membrane to retain tumor cells by filtration with vacuum or centrifugation. Three filters with different pore sizes (0.1, 0.4, and 1.0 microns) were tested. The result showed that all three pore sizes were equally effective in retaining tumor cells by using vacuum filtration. However, the filter with 1.0 micron size pores had the best flow rate. To address the question of upper cell limit, separate filtrations were performed for $10^4$, $10^5$, $10^6$, and $10^7$ cells. In these experiments, it was found that $10^6$ cells could be efficiently vacuum filtered; the rate for filtration of $10^7$ cells became very slow.

TABLE 3

Nucleated Cells in the Buffy Coat and the Whole Blood

| Patient Code | GSOO3 | GSOO4 |
|---|---|---|
| Conc. Nucleated Cells in Buffy Coat (Cells/ml) | $3.35 \times 10^7$ | $5.35 \times 10^7$ |
| Vol. Buffy Coat | 2.5 ml | 3.5 ml |

TABLE 3-continued

Nucleated Cells in the Buffy Coat and the Whole Blood

| Patient Code | GSOO3 | GSOO4 |
|---|---|---|
| Total Nucleated Cells in Buffy Coat | $8.38 \times 10^7$ | $1.87 \times 10^8$ |
| Conc. Nucleated Cells/ml in Whole Blood (Cells/ml) | $4.8 \times 10^6$ | $1.01 \times 10^7$ |
| Vol. Whole Blood | 18 ml | 19 ml |
| Nucleated Cells in Whole Blood | $8.6 \times 10^7$ | $1.92 \times 10^8$ |
| Total Nucleated Cells in Buffy Coat/Blood | 97% | 97% |

TABLE 4

Cancer Cells Detected in Whole Blood and in Buff Coat (WBC$10^7$).

| Patient Code | Exp. Cod | Tumor Cells Detected Using Whole Blood | Tumor Cells Detected Using Buffy Coat |
|---|---|---|---|
| Patient GSOO2 | E453, E455 | 8 (8) | 2 (2) |
| Patient GS003 | E453, E455 | 5 (2,8) | 2 (2) |
| Patient GSOO4 | E453, E455 | 7 (4,10) | 5 (3,7) |

Note: The numbers in the brackets are the actual numbers detected for each sample. The average number of tumor cell detection for each patient is on left side of the brackets.

Blood samples from breast cancer patients were tested for tumor cell detection. Among them were whole blood samples, leukopheresis samples and bone marrow samples. The medical information for all the patients are presented in Table 5. The sensitivity of tumor cell detection in the patients' samples reached 1 tumor cell in $10^8$ PBMC or 1 tumor cell in 10 ml–20 ml of whole blood. Tumor cells were detected in none of the eight healthy individuals, and in 79% of the patient samples. The range of cancer cells detected in those patients who had been through intensive chemotherapy was from 0.5 to 80 tumor cells in 10 ml of blood or 1 to 60 tumor cells in $10^8$ nucleated cells (Table 6).

TABLE 5

Medical Information for Breast Cancer Patients:

| Patient Code | Age | Stage of First Diagnosis | Current Disease Stage | Current Treatment |
|---|---|---|---|---|
| GS001 | 57 | II | IV | Off chemo for 2 y |
| GS002 | 49 | II | IV | chemo. |
| GS003 | 59 | II | IV | Just complete chemo. |
| GS004 | 70 | II | IV | Off chemo for 1 y |
| GS005 | 48 | II | IV | Off chemo/XRT for over 1 y |
| GS006 | 73 | I | IV | Chemo |
| GS007 | 78 | I | IV | Chemo for liver and bone metastasis |
| GS008 | 58 | I | IV | Chemo. |
| GS009 | 64 | II | IV | Off Chem |
| GS010 | N/A | IV | IV | Recently Off chemo |
| GS011 | 75 | II | IV | Chemo |
| GS012 | 42 | II | IV | Chemo |
| GS013 | 83 | II | II | Hormone Rx |
| GS014 | 43 | II | II | None |
| GS015 | 44 | II | II | Adjuvant Chemo |
| GS016 | 86 | II | IV | 3/94 on hormone until 4/95 on taxol |
| GS017 | 76 | III | III | Adjuvant Chemo |
| GS018 | 46 | II | II | Adjuvant Chemo |
| GS019 | 53 | III | III | Chemo, now on Tamoxifen |
| GS020 | 77 | II | II | Ajuvant tamoxifen |
| LP1 (DEB) | N/A | N/A | N/A | N/A |
| LP2 (048627926) | N/A | N/A | N/A | N/A |

TABLE 5-continued

Medical Information for Breast Cancer Patients:

| Patient Code | Age | Stage of First Diagnosis | Current Disease Stage | Current Treatment |
|---|---|---|---|---|
| LP3 (518540804) | N/A | N/A | N/A | N/A |
| LP4 (573620635) | 50 | N/A | IV | N/A |
| LP5 (380882990) | 28 | N/A | III | Mobilization w/GCSF |
| LP6 (574261979) | 41 | II | II | Mobilization w/GCSF, CAF, Chest Irradiat. |
| LP7 (531521249) | 46 | N/A | II | N/A |
| LP8 (539381825) | 54 | II | III | Cyclophosphomide + Doxambicin + GCSF |
| LP9 (575522787) | 44 | III | III | Mobilized with GCSF |
| LP10 (062400767) | 48 | III | IV | Cytoxan, MESNA, Taxol and GCSF |
| LP11 (551604378) | 43 | IV | IV | Cytoxan, Taxol and GCSF |
| BM1 | N/A | N/A | N/A | N/A |

TABLE 9

Tumor Cell Detection in the Peripheral Blood of Normal Individuals and Breast Cancer Patients

| Samples | Blood Vol./Sample | PBMC No. | Tumor Cell Detected | Tumor Cells/ $10^8$ PBMC | Tumor Cells/ 10 ml Blood |
|---|---|---|---|---|---|
| Normal Buffy | 1.46 ml | $10^8$ | 0 | 0 | 0 |
| Normal Buffy | 0.89 ml | $10^8$ | 0 | 0 | 0 |
| Normal Blood | 10.08 ml | $10^8$ | 0 | 0 | 0 |
| Normal Blood | 21.05 ml | $10^8$ | 0 | 0 | 0 |
| Normal Buffy | 2.29 ml | $10^8$ | 0 | 0 | 0 |
| Normal Blood | 7.4 ml | $10^8$ | 0 | 0 | 0 |
| Normal Buffy | 1.0 ml | $10^8$ | 0 | 0 | 0 |
| Normal Buffy | 2.1 ml | $10^8$ | 0 | 0 | 0 |
| Normal Buffy | 1.1 ml | $10^8$ | 0 | 0 | 0 |
| Normal Buffy | 2.0 ml | $10^8$ | 0 | 0 | 0 |
| Normal Buffy | 0.263 ml | $10^7$ | 0 | 0 | 0 |
| Normal Buffy | 0.323 ml | $3 \times 10^7$ | 0 | 0 | 0 |
| Normal Buffy | 0.24 ml | $3 \times 10^7$ | 0 | 0 | 0 |
| Normal Buffy | 0.30 ml | $3 \times 10^7$ | 0 | 0 | 0 |
| Normal Buffy | 0.485 ml | $3 \times 10^7$ | 0 | 0 | 0 |
| Normal Buffy | 0.30 ml | $3 \times 10^7$ | 0 | 0 | 0 |
| GS001 Buffy | 0.24 ml | $10^7$ | 5 | 50 | 21 |
| GS001-2 Bl. | 20.83 ml | $5 \times 10^7$ | 0 | 0 | 0 |
| GS001-3 Bl. | 13.99 ml | $10^8$ | 14 | 14 | 10 |
| GS002 Blood | 0.625 ml | $10^7$ | 5 | 50 | 80 |
| HS003 Blood | 2.8 ml | $10^7$ | 4 | 40 | 14 |
| GS003-2 Bl. | 2 ml | $10^7$ | 2 | 20 | 10 |
| GS004 Blood | 0.995 ml | $10^7$ | 6 | 60 | 60 |
| GS004-2 Bl. | 0.9 ml | $10^7$ | 18 | 180 | 200 |
| GS005 Blood | 12.35 ml | $10^8$ | 1 | 1 | 1 |
| HS005-2 Bl. | 9.09 ml | $10^8$ | 5 | 5 | 6 |
| GS006 Blood | 14.39 ml | $10^8$ | 1.5 | 1.5 | 1 |
| GS006-2 Bl. | 22.73 ml | $5 \times 10^7$ | 6 | 12 | 3 |
| GS007 Blood | 16.0 ml | $10^8$ | 0 | 0 | 0 |
| GS008-2 Bl. | 25.0 ml | $1.25 \times 10^8$ | 1 | 0.8 | 0.4 |
| GS008 Blood | 16.7 ml | $10^8$ | 0 | 0 | 0 |
| GS009 Blood | 1.25 ml | $10^7$ | 2 | 20 | 16 |
| GS010 Blood | 13.9 ml | $10^8$ | 0 | 0 | 0 |
| GS011 Blood | 8.6 ml | $5 \times 10^7$ | 1 | 2 | 1 |
| GS012 Blood | 20.8 ml | $5 \times 10^7$ | 1 | 2 | 0.5 |
| GS013 Blood | 20.8 ml | $10^8$ | 10 | 10 | 5 |
| GS014 Blood | 9.09 ml | $10^8$ | 3 | 3 | 3 |
| GS015 Blood | 21.67 ml | $1.3 \times 10^8$ | 0 | 0 | 0 |
| GS016 Blood | 25.01 ml | $1.2 10^8$ | 7 | 6 | 0.3 |
| GS017 Blood | 14.09 ml | $11.6 \times 10^7$ | 1 | 9 | 0.7 |
| GS018 Blood | 9.30 ml | $6.64 \times 10^7$ | 3 | 5 | 3 |
| GS019 Blood | 11.89 ml | $10.4 \times 10^7$ | 0 | 0 | 0 |

TABLE 9-continued

Tumor Cell Detection in Leukapheresis Samples of Breast Cancer Patients

| Samples | Blood Vol./Sample | PBMC No. | Tumor Cell Detected | Tumor Cells $10^8$ PBMC |
|---|---|---|---|---|
| LP1 | 0.60 ml | $10^8$ | 10 | 10 |
| LP2 | 0.44 ml | $5 \times 10^7$ | 2 | 4 |
| Lp3 | 1.09 ml | $5 \times 10^7$ | 18 | 36 |
| LP4 | 0.10 ml | $10^7$ | 9 | 90 |
| LP5 | 0.50 ml | $5 \times 10^7$ | 19 | 38 |
| LP6 | 0.478 ml | $10^8$ | 18 | 18 |
| LP7 | 1.944 ml | $6.4 \times 10^7$ | 1 | 2 |
| LP8 | 2.00 ml | $1.09 \times 10^6$ | 5 | 459 |
| LP9 | 2.00 ml | $1.08 \times 10^7$ | 1 | 10 |
| LP10 | 2.00 ml | $6.5 \times 10^6$ | 0 | 0 |
| LP11 | 1.15 ml | $8.92 \times 10^6$ | 9 | 100 |

Tumor Cell Detection in the Bone Marrow of Brest Cancer Patients

| BM1 | 11.77 ml | $5 \times 10^7$ | 3 | 6 |
| BM2 | 2.0 ml | $1.6 \times 10^8$ | 1 | 0.6 |

The above data demonstrate a carcinoma cell detection assay that can isolate and visualize cancer cells in peripheral blood and bone marrow. The sensitivity of the assay reaches one cancer cell in $10^8$ nucleated cells of peripheral blood. The average recovery of cancer cells is approximately 75%, and the assay is consistent and reproducible.

The tumor cell detection assay was applied to breast cancer patients. Tests for the detection of cancer cells from forty breast cancer patients with stage II–IV diseases were performed. Among them, 26 were peripheral blood, 12 were leukapheresis and two were bone marrow. The sensitivity of tumor cell detection in patient samples was one tumor cell in 10–20 ml of whole blood. No tumor cells were found in any of the 16 healthy individuals. Tumor cells were detected in 80% of the patient samples. The range of cancer cells detected was from 1 to 600 tumor cells in $10^8$ nucleated cells. A correlation was found between the frequency of tumor cells and the disease stage and patient age.

It is evident from the above results that the subject invention provides for a simple, fast method for separating disseminated tumor cells from hematopoietic cells. The fraction of cells that is enriched for tumor cells is useful for quantitation of tumor cells, and for further cell phenotyping. The ease of operation, and ability to scale up the number and size of samples provides significant benefits over existing methods.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for separation of disseminated tumor cells from a whole blood cell sample present as a fluid suspension, the method comprising the steps, in order, of:
   adding to said whole blood cell sample antibodies specific for one or more antigens expressed by said tumor cells and absent on blood cells, wherein said antibodies are coupled to a magnetically responsive reagent, under conditions sufficient to specifically bind said coupled antibodies to said antigens;
   passing said sample through a ferromagnetic matrix in the presence of a magnetic field to magnetically immobilize cells in the sample having coupled antibodies bound thereto;
   washing said matrix of unbound cells; and
   removing the magnetic field and eluting bound cells from said matrix directly onto a solid support to provide an enriched cell sample comprising tumor cells, wherein said eluting is by centrifugation or vacuum filtration.

2. The method of claim 1, wherein said solid support is a polycarbonate filter or a slide.

3. The method of claim 1, wherein said tumor cells are carcinoma cells.

4. The method of claim 3, wherein said carcinoma cells are from a carcinoma having a primary site in breast, ovary, endometrium, cervix, colon, stomach or lung tissue.

5. The method of claim 1, wherein said coupled antibodies are specific for one or more antigens selected from the group consisting of epithelial membrane antigen, human embryonic antigen, human milk fat globules, MBr1, MBr8, Ber-EP4, 17-1A, C26, and T16.

6. A method for separation of disseminated tumor cells from a whole blood cell sample present as a fluid suspension, the method comprising the steps, in order, of:
   adding to said whole blood cell sample antibodies specific for one or more antigens expressed by said tumor cells and absent on blood cells, wherein said antibodies are coupled to a magnetically responsive reagent, under conditions sufficient to specifically bind said coupled antibodies to said antigens;
   passing said sample through a ferromagnetic matrix in the presence of a magnetic field to magnetically immobilize cells in the sample having coupled antibodies bound thereto;
   washing said matrix of unbound cells; and
   removing the magnetic field and eluting bound cells from said matrix directly onto a solid support to provide an enriched cell sample comprising tumor cells, wherein said solid support is a filter and said eluting is by filtration through said filter, to thereby deposit said eluted cells directly thereon.

7. The method of claim 6, wherein said solid support is a polycarbonate filter.

8. The method of claim 6, wherein said tumor cells are carcinoma cells.

9. The method of claim 6, wherein said carcinoma cells are from a carcinoma having a primary site in breast, ovary, endometrium, cervix, colon, stomach or lung tissue.

10. The method of claim 6, wherein said coupled antibodies are specific for one or more antigens selected from the group consisting of epithelial membrane antigen, human embryonic antigen, human milk fat globules, MBr1, MBr8, Ber-EP4, 17-1A, C26, and T16.

11. A method for separation of disseminated tumor cells from a whole blood cell sample present as a fluid suspension, the method comprising the steps, in order, of:

provo a sample comprising whole blood cells present as a fluid suspension;

permeabilizing said cell suspension;

fixing said permeabilized cell suspension;

adding to said permeabilized fixed cell suspension antibodies specific for one or more antigens expressed by said tumor cells and absent on blood cells, wherein said antibodies are coupled to a magnetically responsive reagent, under conditions sufficient to specifically bind said coupled antibodies to said antigens;

passing said suspension through a ferromagnetic matrix in the presence of a magnetic field to magnetically immobilize cells in the suspension having coupled antibodies bound thereto;

washing said matrix of unbound cells; and removing the magnetic field and eluting bound cells from said matrix directly onto a solid support to provide an enriched cell sample comprising tumor cells, wherein said solid support is a filter and said eluting is by filtration through said filter, to thereby deposit said eluted cells directly thereon.

12. The method of claim 11 wherein said coupled antibodies are specific for cytokeratin.

* * * * *